United States Patent [19]
Hotz et al.

[11] 3,958,974
[45] May 25, 1976

[54] HERBICIDAL N-ARYL SUBSTITUTED AZETIDINONES

[75] Inventors: Roger D. Hotz, Evanston; John Krenzer, Oak Park, both of Ill.

[73] Assignee: Velsicol Chemical Corporation, Chicago, Ill.

[22] Filed: Dec. 20, 1974

[21] Appl. No.: 534,596

[52] U.S. Cl. ................................ 71/88; 260/239 A
[51] Int. Cl.² ............................................ A01N 9/22
[58] Field of Search .................... 71/88; 260/239 A

[56] References Cited
UNITED STATES PATENTS

| | | | |
|---|---|---|---|
| 3,567,711 | 3/1971 | Van Pappen | 71/88 X |
| 3,637,746 | 1/1972 | Wei et al. | 260/239 A |
| 3,764,624 | 10/1973 | Strong et al. | 71/88 X |
| 3,840,569 | 8/1974 | Beck | 71/88 X |

OTHER PUBLICATIONS
Manhas et al. Chem Abst. Vol. 68 (1968) 58967r.
Blackburn et al. Chem. Abst. Vol. 77 (1972) 87404w.
Merger, Chem. Abst. Vol. 77 (1972) 61977k.
Merger, Chem. Abst. Vol. 76 (1972) 3683e.

*Primary Examiner*—Lewis Gotts
*Assistant Examiner*—Catherine L. Mills
*Attorney, Agent, or Firm*—Robert J. Schwarz; Dietmar H. Olesch

[57] ABSTRACT

Disclosed are herbicidal compositions comprising an inert carrier and as an essential active ingredient in a quantity toxic to weeds a compound of the formula wherein X is selected from the group consisting of alkyl, alkenyl, alkoxy, alkylthio, halogen, haloalkyl and nitro; and $n$ is an integer from 0 to 5.

8 Claims, No Drawings

HERBICIDAL N-ARYL SUBSTITUTED AZETIDINONES

This invention relates to herbicidal compositions comprising an inert carrier and as an essential active ingredient in a quantity toxic to weeds a compound of the formula

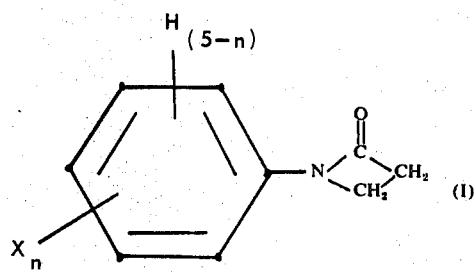

wherein X is selected from the group consisting of alkyl, alkenyl, alkoxy, alkylthio, halogen, haloalkyl and nitro; and $n$ is an integer from 0 to 5.

In a preferred embodiment of this invention X is in the 3 and/or 4 position and selected from the group consisting of lower alkyl, lower alkenyl, lower alkoxy, lower alkylthio, halogen, chloroalkyl, bromoalkyl, trifluoromethyl and nitro.

The term lower as used herein designates a straight or branched carbon chain of up to six carbon atoms.

The compounds of the present invention can be prepared by reacting a compound of the formula

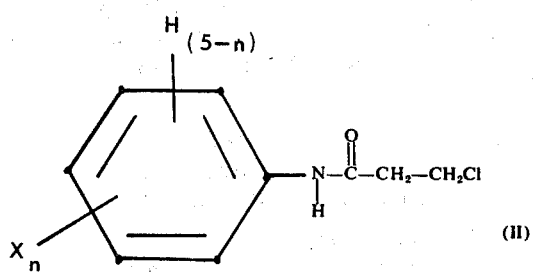

wherein X and $n$ are as heretofore described, with an equimolar or excess molar amount of the compound of the formula

This reaction can be effected by slowly adding a solution of the compound of formula II in an inert solvent such as carbon tetrachloride to a solution of the compound of formula III in dimethyl sulfoxide. The compound of formula III can be freshly prepared in situ by combining the appropriate molar amount of sodium hydride with an excess molar amount of dimethyl sulfoxide and stirring the mixture until no further hydrogen gas evolves. During the addition of the compound of formula II to the compound of formula III the reaction mixture is maintained at room temperature or below room temperature such as from 10° to 30°C by cooling. After the addition is completed the reaction mixture is stirred for a period of up to about 4 hours to ensure completion of the reaction. After this time the reaction mixture can be washed with water and with aqueous sodium bicarbonate, dried over anhydrous magnesium sulfate and filtered. The filtrate can then be stripped of solvent under reduced pressure to yield the desired product as the residue.

The compounds of formula II when not readily available can be conveniently prepared by reacting an aniline of the formula

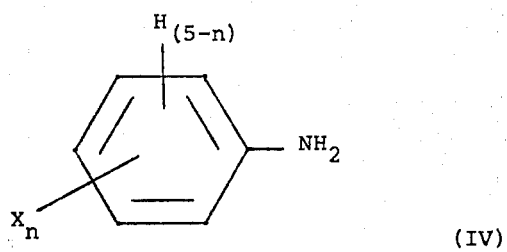

wherein X and $n$ are as heretofore described, with $\beta$-chloropropionyl chloride. This reaction can be effected by combining about equimolar amounts of the aniline of formula IV and $\beta$-chloropropionyl chloride in an inert organic reaction medium such as benzene and heating the resulting mixture at reflux for a period of from ½ to about 6 hours. After this time the reaction mixture can be washed with water and aqueous sodium bicarbonate, dried over anhydrous magnesium sulfate and filtered. The filtrate is then stripped of solvent under reduced pressure to yield the desired product.

Exemplary suitable anilines of formula IV useful in preparing the compounds of the present invention are 3-methylaniline, 3-ethylaniline, 4-propylaniline, 3,4-dimethylaniline, 3,4-diethylaniline, 4-butylaniline, 4-hexylaniline, 3-allylaniline, 4-pent-3-enylaniline, 4-hex-4-enylaniline, 3-methoxyaniline, 4-ethoxyaniline, 3-propoxyaniline, 2-hexyloxyaniline, 4-methylthioaniline, 3-ethylthioaniline, 3-propylthioaniline, 4-hexylthioaniline, 3-chloroaniline, 3,4-dichloroaniline, 4-fluoroaniline, 4-iodoaniline, 3,4-dibromoaniline, 2,4,6-trichloroaniline, 2,6-dichloro-4-nitroaniline, 4-trifluoromethylaniline, 2-bromomethylaniline, 4-δ-chlorobutylaniline, 3,4-dinitroaniline, 2-methyl-4-chloroaniline, 3,4-dimethoxyaniline, 2-methoxy-3,6-dichloroaniline and the like.

The manner in which the compounds of the present invention can be prepared is more specifically illustrated in the following examples.

EXAMPLE 1

Preparation of N-(3,4-Dimethylphenyl)-$\beta$-chloropropionamide 3,4-Dimethylaniline (25.5 grams), $\beta$-chloropropionyl chloride (20 grams) and benzene (100 ml) are charged into a glass reaction flask equipped with a mechanical stirrer, thermometer and reflux condenser. The reaction mixture is stirred at reflux for a period of about 3 hours. After this time the reaction mixture is cooled to room temperature and is washed with aqueous sodium bicarbonate, dilute hydrochloric acid and water. The washed mixture is then dried over anhydrous magnesium sulfate, is filtered and stripped of benzene under reduced pressure to yield the desired product N-(3,4-dimethylphenyl)-β-chloropropionamide as the residue.

EXAMPLE 2

Preparation of N-(3,4-Dimethylphenyl)-2-azetidinone

Sodium hydride (2.4 grams; 57% dispersion in mineral oil) is charged into a glass reaction flask. The mineral oil is removed by washing the sodium hydride with benzene and then dimethyl sulfoxide (50 ml) is slowly added with stirring. The mixture is stirred until no more hydrogen gas evolves. A solution of N-(3,4-dimethylphenyl)-β-chloropropionamide (19.8 grams) in carbon tetrachloride (50 ml) is added dropwise to the reaction flask with stirring while maintaining the temperature of the reaction mixture below about 30°C. After the addition is completed the reaction mixture is allowed to stand at room temperature for a period of about 8 hours. After this time benzene is added and the reaction mixture is then washed with water and aqueous sodium bicarbonate. The washed mixture is then dried over anhydrous magnesium sulfate, is filtered, and is stripped of solvents to yield the desired product N-(3,4-dimethylphenyl)-2-azetidinone.

EXAMPLE 3

Preparation of
N-(3,4-Dichlorophenyl)-β-chloropropionamide 3,4-Dichloroaniline (25.5 grams), β-chloropropionyl chloride (20 grams) and benzene (100 ml) are charged into a glass reaction vessel equipped with a mechanical stirrer, thermometer and reflux condenser. The reaction mixture is heated at reflux with stirring for a period of about 3 hours. After this time the reaction mixture is cooled to room temperature and is washed with dilute aqueous sodium bicarbonate, with dilute hydrochloric acid and with water. The washed mixture is then dried over anhydrous magnesium sulfate, filtered and stripped of benzene under reduced pressure to yield the desired product N-(3,4-dichlorophenyl)-β-chloropropionamide as the residue.

EXAMPLE 4

Preparation of N-(3,4-Dichlorophenyl)-2-azetidinone

Sodium hydride (2.4 grams; 57% dispersion in mineral oil) is charged into a glass reaction flask. The mineral oil is removed by washing the sodium hydride with benzene, and dimethyl sulfoxide (50 ml) is thereafter slowly added with stirring. The mixture is stirred until no more hydrogen gas evolves. A solution of N-(3,4-dichlorophenyl)-β-chloropropionamide (19.8 grams) in carbon tetrachloride (50 ml) is added dropwise to the reaction flask with stirring while maintaining the temperature of the reaction mixture below about 30°C. After the addition is completed the reaction mixture is allowed to stand at room temperature for a period of about 8 hours. After this time benzene is added and the reaction mixture is washed with water and aqueous sodium bicarbonate. The washed mixture is then dried over anhydrous magnesium sulfate, is filtered, and is stripped of solvents under reduced pressure to yield the desired product N-(3,4-dichlorophenyl)-2-azetidinone as a solid residue having a melt point of 139° to 142°C.

EXAMPLE 5

Preparation of
N-(3-Allylphenyl)-β-chloropropionamide

3-Allylaniline (0.3 moles), β-chloropropionyl chloride (0.35 mole) and benzene (100 ml) are charged into a glass reaction vessel equipped with a mechanical stirrer, thermometer and reflux condenser. The reaction mixture is heated at reflux with stirring for a period of about 4 hours. After this time the reaction mixture is cooled to room temperature and is washed with dilute aqueous sodium bicarbonate, with dilute hydrochloric acid and with water. The washed mixture is then dried over anhydrous magnesium sulfate, filtered and stripped of benzene under reduced pressure to yield the desired product N-(3-allylphenyl)-β-chloropropionamide as the residue.

EXAMPLE 6

Preparation of N-(3-Allylphenyl)-2-azetidinone

Sodium hydride (0.1 mole; 57% dispersion in mineral oil) is charged into a glass reaction flask. The mineral oil is removed by washing the sodium hydride with benzene, and dimethyl sulfoxide (50 ml) is thereafter slowly added with stirring. The mixture is stirred until no more hydrogen gas evolves. A solution of N-(3-allylphenyl)-β-chloropropionamide (0.08 mole) in carbon tetrachloride (50 ml) is added dropwise to the reaction flask with stirring while maintaining the temperature of the reaction mixture below about 30°C. After the addition is completed the reaction mixture is allowed to stand at room temperature for a period of about 8 hours. After this time benzene is added and the reaction mixture is washed with water and aqueous sodium bicarbonate. The washed mixture is then dried over anhydrous magnesium sulfate, is filtered, and is stripped of solvents under reduced pressure to yield the desired product N-(3-allylphenyl)-2-azetidinone as the residue.

EXAMPLE 7

Preparation of
N-(3,4-Dimethoxyphenyl)-β-chloropropionamide 3,4-Dimethoxyaniline (0.3 mole), β-chloropropionyl chloride (0.35 mole) and benzene (100 ml) are charged into a glass reaction vessel equipped with a mechanical stirrer, thermometer and reflux condenser. The reaction mixture is heated at reflux with stirring for a period of about 5 hours. After this time the reaction mixture is cooled to room temperature and is washed with dilute aqueous sodium bicarbonate, with dilute hydrochloric acid and with water. The washed mixture is then dried over anhydrous magnesium sulfate, filtered and stripped of benzene under reduced pressure to yield the desired product N-(3,4-dimethoxyphenyl)-β-chloropropionamide as the residue.

EXAMPLE 8

Preparation of
N-(3,4-Dimethoxyphenyl)-2-azetidinone

Sodium hydride (0.1 mole; 57% dispersion in mineral oil) is charged into a glass reaction flask. The mineral oil is removed by washing the sodium hydride with benzene, and dimethyl sulfoxide (50 ml) is thereafter slowly added with stirring. The mixture is stirred until no more hydrogen gas evolves. A solution of N-(3,4- dimethoxyphenyl)-β-chloropropionamide (0.08 mole) in carbon tetrachloride (50 ml) is added dropwise to the reaction flask with stirring while maintaining the temperature of the reaction mixture below about 30°C. After the addition is completed the reaction mixture is allowed to stand at room temperature for a period of about 8 hours. After this time benzene is added and the reaction mixture is washed with water and aqueous sodium bicarbonate. The washed mixture is then dried over anhydrous magnesium sulfate, is filtered, and is stripped of solvents under reduced pressure to yield the desired product N-(3,4-dimethoxyphenyl)-2-azetidinone as the residue.

EXAMPLE 9

Preparation of N-(3-Methylthiophenyl)-β-chloropropionamide

3-Methylthioaniline (0.3 mole), β-chloropropionyl chloride (0.35 mole) and benzene (100 ml) are charged into a glass reaction vessel equipped with a mechanical stirrer, thermometer and reflux condenser. The reaction mixture is heated at reflux with stirring for a period of about 3 hours. After this time the reaction mixture is cooled to room temperature and is washed with dilute aqueous sodium bicarbonate, with dilute hydrochloric acid and with water. The washed mixture is then dried over anhydrous magnesium sulfate, filtered and stripped of benzene under reduced pressure to yield the desired product N-(3-methylthiophenyl)-β-chloropropionamide as the residue.

EXAMPLE 10

Preparation of N-(3-Methylthiophenyl)-2-azetidinone

Sodium hydride (0.1 mole; 57% dispersion in mineral oil) is charged into a glass reaction flask. The mineral oil is removed by washing the sodium hydride with benzene, and dimethyl sulfoxide (50 ml) is thereafter slowly added with stirring. The mixture is stirred until no more hydrogen gas evolves. A solution of N-(3-methylthiophenyl)-β-chloropropionamide (0.08 mole) in carbon tetrachloride (50 ml) is added dropwise to the reaction flask with stirring while maintaining the temperature of the reaction mixture below about 30°C. After the addition is completed the reaction mixture is allowed to stand at room temperature for a period of about 8 hours. After this time benzene is added and the reaction mixture is washed with water and aqueous sodium bicarbonate. The washed mixture is then dried over anhydrous magnesium sulfate, is filtered, and is stripped of solvents under reduced pressure to yield the desired product N-(3-methylthiophenyl)-2-azetidinone as the residue.

EXAMPLE 11

Preparation of N-(4-Trifluoromethylphenyl)-β-chloropropionamide

4-Trifluoromethylaniline (0.3 mole), β-chloropropionyl chloride (0.35 mole) and benzene (100 ml) are charged into a glass reaction vessel equipped with a mechanical stirrer, thermometer and reflux condenser. The reaction mixture is heated at reflux with stirring for a period of about 3 hours. After this time the reaction mixture is cooled to room temperature and is washed with dilute aqueous sodium bicarbonate, with dilute hydrochloric acid and with water. The washed mixture is then dried over anhydrous magnesium sulfate, filtered and stripped of benzene under reduced pressure to yield the desired product N-(4-trifluoromethylphenyl)-β-chloropropionamide as the residue.

EXAMPLE 12

Preparation of N-(4-Trifluoromethylphenyl)-2-azetidinone

Sodium hydride (0.1 mole; 57% dispersion in mineral oil) is charged into a glass reaction flask. The mineral oil is removed by washing the sodium hydride with benzene, and dimethyl sulfoxide (50 ml) is thereafter slowly added with stirring. The mixture is stirred until no more hydrogen gas evolves. A solution of N-(4-trifluoromethylphenyl)-β-chloropropionamide (0.08 mole) in carbon tetrachloride (50 ml) is added dropwise to the reaction flask with stirring while maintaining the temperature of the reaction mixture below about 30°C. After the addition is completed the reaction mixture is allowed to stand at room temperature for a period of about 8 hours. After this time benzene is added and the reaction mixture is washed with water and aqueous sodium bicarbonate. The washed mixture is then dried over anhydrous magnesium sulfate, is filtered, and is stripped of solvents under reduced pressure to yield the desired product N-(4-trifluoromethylphenyl)-2-azetidinone as the residue.

EXAMPLE 13

Preparation of N-(3-Nitrophenyl)-β-chloropropionamide

3-Nitroaniline (0.3 moles), β-chloropropionyl chloride (0.35 mole) and benzene (100 ml) are charged into a glass reaction vessel equipped with a mechanical stirrer, thermometer and reflux condenser. The reaction mixture is heated at reflux with stirring for a period of about 4 hours. After this time the reaction mixture is cooled to room temperature and is washed with dilute aqueous sodium bicarbonate, with dilute hydrochloric acid and with water. The washed mixture is then dried over anhydrous magnesium sulfate, filtered and stripped of benzene under reduced pressure to yield the desired product N-(3-nitrophenyl)-β-chloropropionamide as the residue.

EXAMPLE 14

Preparation of N-(3-Nitrophenyl)-2-azetidinone

Sodium hydride (0.1 mole; 57% dispersion in mineral oil) is charged into a glass reaction flask. The mineral oil is removed by washing the sodium hydride with benzene, and dimethyl sulfoxide (50 ml) is thereafter slowly added with stirring. The mixture is stirred until no more hydrogen gas evolves. A solution of N-(3-nitrophenyl)-β-chloropropionamide (0.08 mole) in carbon tetrachloride (50 ml) is added dropwise to the reaction flask with stirring while maintaining the temperature of the reaction mixture below about 30°C. After the addition is completed the reaction mixture is allowed to stand at room temperature for a period of about 8 hours. After this time benzene is added and the reaction mixture is washed with water and aqueous sodium bicarbonate. The washed mixture is then dried over anhydrous magnesium sulfate, is filtered, and is stripped of solvents under reduced pressure to yield the desired product N-(3-nitrophenyl)-2-azetidinone as the residue.

Additional compounds within the scope of the present invention which can be prepared by the procedures detailed in the foregoing examples are N-(3,4-diethylphenyl)-2-azetidinone, N-(3,4-dipropylphenyl)-2-azetidinone, N-(4-butylphenyl)-2-azetidinone, N-(4-pentylphenyl)-2-azetidinone, N-(3-hexylphenyl)-2-azetidinone, N-(3-but-3-enylphenyl)-2-azetidinone, N-(4-pent-4-enylphenyl)-2-azetidinone, N-(4-hex-4-enylphenyl)-2-azetidinone, N-(3,4-diethoxyphenyl)-2-azetidinone, N-(2-propoxyphenyl)-2-azetidinone, N-(4-butyloxyphenyl)-2-azetidinone, N-(4-hexyloxyphenyl)-2-azetidinone, N-(3,4-dimethylthiophenyl)-2-azetidinone, N-(4-ethylthiophenyl)-2-azetidinone, N-(3-propylthiophenyl)-2-azetidinone, N-(4-butylthiophenyl)-2-azetidinone, N-(4-hexylthiophenyl)-2-azetidinone, N-(3,4-difluorophenyl)-2-azetidinone, N-(3,4-diiodophenyl)-2-azetidinone, N-(3,4-dibromophenyl)-2-azetidinone, N-(2,6-difluorophenyl)-2-azetidinone, N-(2,4,6-trichlorophenyl)-2-azetidinone, N-(4-chloromethylphenyl)-2-azetidinone, N-(3-$\beta$-bromoethylphenyl)-2-azetidinone, N-(4-$\gamma$-bromopropylphenyl)-2-azetidinone, N-(3-$\beta,\beta,\beta$-trichloroethylphenyl)-2-azetidinone, N-(3,4-dinitrophenyl)-2-azetidinone, N-(2-methyl-4-chlorophenyl)-2-azetidinone, N-(3-methyl-4-fluorophenyl)-2-azetidinone, N-(3-methyl-4-nitrophenyl)-2-azetidinone, N-(3-methoxy-4-chlorophenyl)-2-azetidinone and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

Example 15

| Preparation of a Dust | |
|---|---|
| Product of Example 2 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. With the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as 4-(chloroacetyl)morpholine, 1-(chloroacetyl)piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, wintercress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal activity of the compounds of this invention was demonstrated by an experiment carried out for the post-emergence control of a variety of weeds. In this experiment the compound to be tested was formulated as an aqueous emulsion and sprayed at the indicated dosage on the foliage of the weeds that have attained a prescribed size. After spraying the plants were placed in a greenhouse and watered daily or more frequently. Water was not applied to the foliage of the treated plants. The severity of the injury was determined 14 days after treatment and was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of these compounds is demonstrated by the following data:

TABLE I

| Weed Species | Injury Rating Product of Example 4 Rate (lbs./acre) 10 |
|---|---|
| Yellow Nutsedge | 2 |
| Wild Oats | 4 |
| Jimsonweed | 9 |
| Pigweed | 10 |
| Johnsongrass | 5 |
| Bindweed | 2 |
| Mustard | 9 |
| Yellow Foxtail | 9 |
| Barnyardgrass | 9 |
| Crabgrass | 7 |
| Morningglory | 9 |

We claim:
1. A method of controlling weeds which comprises contacting the weeds with a herbicidal composition comprising an inert carrier and as an essential active ingredient in a quantity toxic to weeds a compound of the formula

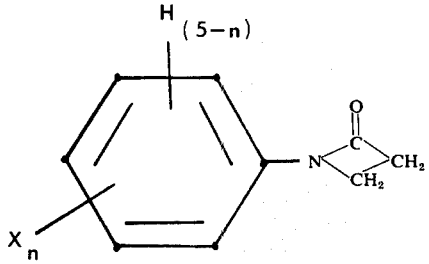

wherein X is selected from the group consisting of lower alkyl, lower alkenyl, lower alkoxy, lower alkylthio, halogen, lower haloalkyl and nitro; and n is an integer from 0 to 5.

2. The method of claim 1 wherein the compound is N-(3,4-dimethylphenyl)-2-azetidinone.

3. The method of claim 1 wherein the compound is N-(3,4-dichlorophenyl)-2-azetidinone.

4. The method of claim 1 wherein the compound is N-(3-allylphenyl)-2-azetidinone.

5. The method of claim 1 wherein the compound is N-(3,4-dimethoxyphenyl)-2-azetidinone.

6. The method of claim 1 wherein the compound is N-(3-methylthiophenyl)-2-azetidinone.

7. The method of claim 1 wherein the compound is N-(4-trifluoromethylphenyl)-2-azetidinone.

8. The method of claim 1 wherein the compound is N-(3,4-dibromophenyl)-2-azetidinone.

* * * * *